United States Patent
Hinds et al.

(10) Patent No.: US 10,322,297 B1
(45) Date of Patent: Jun. 18, 2019

(54) ELECTRICALLY PASSIVE LOW-LEVEL LIGHT THERAPY SYSTEM AND METHODS INCORPORATING SAME

(71) Applicant: Lumia Group, LLC, Charlotte, NC (US)

(72) Inventors: Robert Gates Hinds, Charlotte, NC (US); Marco Scipioni, Charlotte, NC (US)

(73) Assignee: Lumia Group, LLC, Charlotte, NC (US)

( * ) Notice: Subject to any disclaimer, the term of this patent is extended or adjusted under 35 U.S.C. 154(b) by 0 days.

(21) Appl. No.: 16/127,463

(22) Filed: Sep. 11, 2018

Related U.S. Application Data

(60) Provisional application No. 62/720,544, filed on Aug. 21, 2018.

(51) Int. Cl.
| | |
|---|---|
| *G02B 3/00* | (2006.01) |
| *H01L 31/055* | (2014.01) |
| *A61N 5/06* | (2006.01) |
| *A61B 5/00* | (2006.01) |

(52) U.S. Cl.
CPC .......... *A61N 5/0616* (2013.01); *A61B 5/6804* (2013.01); *A61B 5/6803* (2013.01); *A61N 2005/063* (2013.01); *A61N 2005/0645* (2013.01); *A61N 2005/0651* (2013.01);
(Continued)

(58) Field of Classification Search
CPC .... G02B 3/00; G02B 5/02; G02F 1/01; H01L 31/054; H01L 31/055
USPC ......... 136/257; 359/288, 599, 642; 428/221, 428/373, 411.1
See application file for complete search history.

(56) References Cited

U.S. PATENT DOCUMENTS

| | | |
|---|---|---|
| 8,084,377 B2 | 12/2011 | Kreindel et al. |
| 2005/0111813 A1 | 5/2005 | Hajto et al. |
| 2006/0041039 A1 | 2/2006 | Fenyvesi et al. |

(Continued)

FOREIGN PATENT DOCUMENTS

WO   2009/154473 A2   12/2009

OTHER PUBLICATIONS

Press Release for Quantum Bio-Medicals Ltd., "Photo Therapeutic Medical Garment, Wearable full body skin solution, Regeneration Medication", HongKong, Jan. 13, 2013.
(Continued)

*Primary Examiner* — Carl H Layno
*Assistant Examiner* — Jon Eric C Morales
(74) *Attorney, Agent, or Firm* — Morgan, Lewis & Bockius LLP

(57) ABSTRACT

Low-level light therapy system with an electrically passive, article of apparel that absorbs an incident spectrum including one or more of a UV wavelength, a visible wavelength, and a near infrared wavelength and emits light having an emission spectrum including visible light radiation and near infrared radiation. Light is emitted from the yarns and a textile material consisting of a network of yarns (as well as the article of apparel made from such a textile material) having an emission spectrum including visible light radiation and near infrared radiation in a direction toward a body of a person. An article of apparel that emits light in the visible/near infrared spectrum, a method of manufacture, and a low-level light therapy method are also disclosed.

37 Claims, 12 Drawing Sheets

(52) U.S. Cl.
CPC ............... *A61N 2005/0659* (2013.01); *A61N 2005/0661* (2013.01); *A61N 2005/0662* (2013.01)

(56) References Cited

U.S. PATENT DOCUMENTS

| | | |
|---|---|---|
| 2011/0284729 A1 | 11/2011 | Abouraddy et al. |
| 2012/0024345 A1 | 2/2012 | Reisfeld et al. |
| 2012/0060897 A1 | 3/2012 | Bomm et al. |
| 2015/0177423 A1* | 6/2015 | Scipioni .............. H01L 31/0543 136/257 |

OTHER PUBLICATIONS

Driggers (edited by), "Encyclopedia of Optical Engineering; Fourier Transform Infrared Spectroscopy", Marcel Dekker, Inc., New York Basel, 2003, pp. 607-614.

Verbunt et al., "Increased efficiency of luminescent solar concentrators after application of organic wavelength selective mirrors", Optics Express, vol. 20, No. S5, published Jul. 18, 2012, pp. A655-A668.

\* cited by examiner

FIG. 8
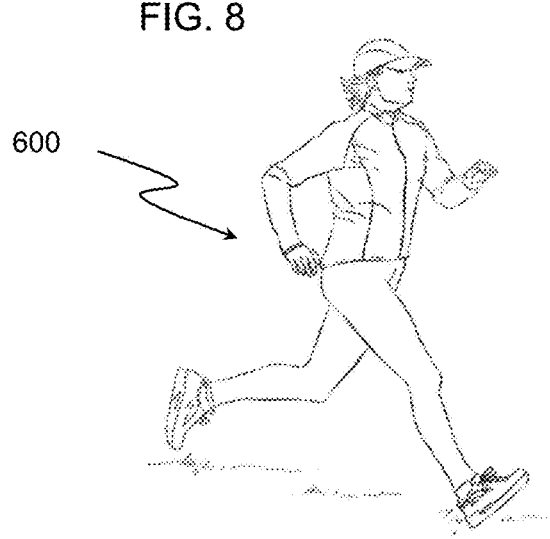
FIG. 9
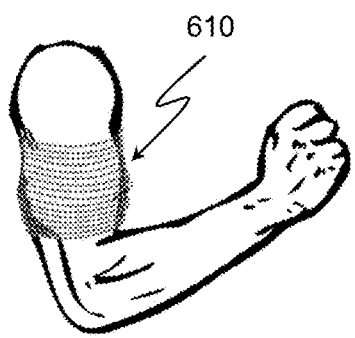
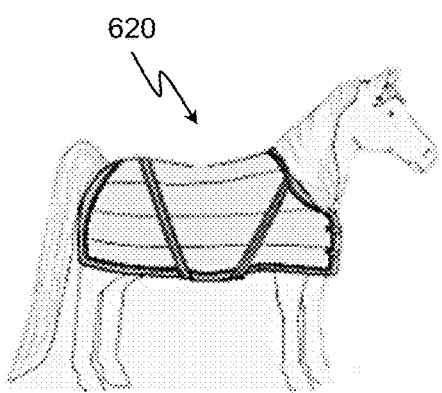
FIG. 10

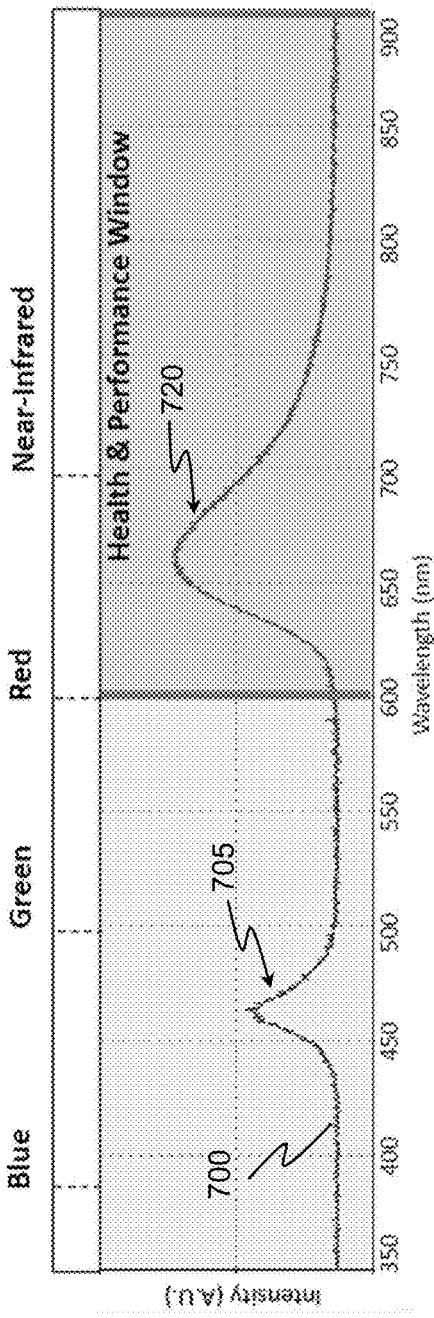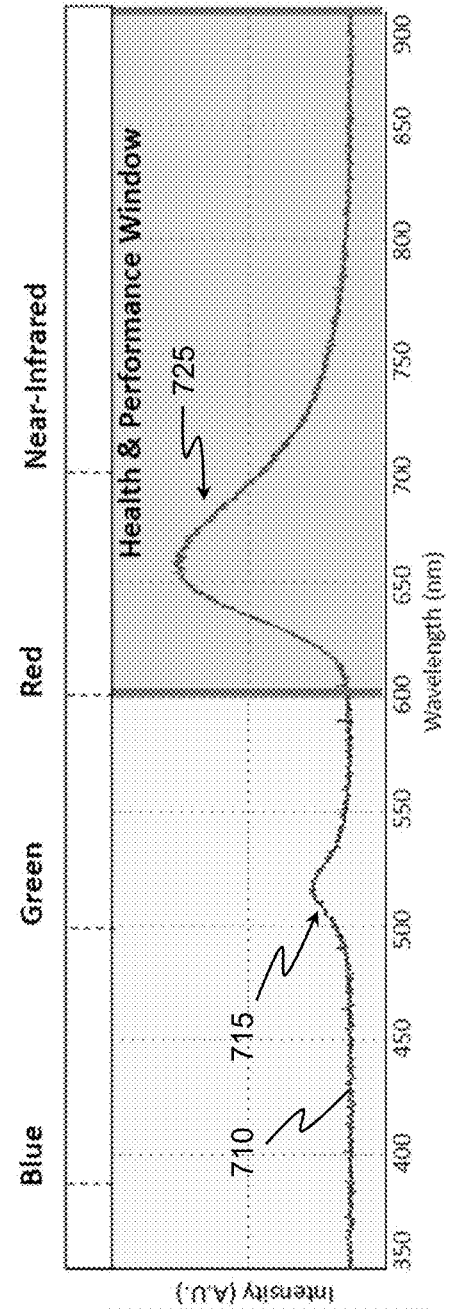
FIG. 11A
FIG. 11B

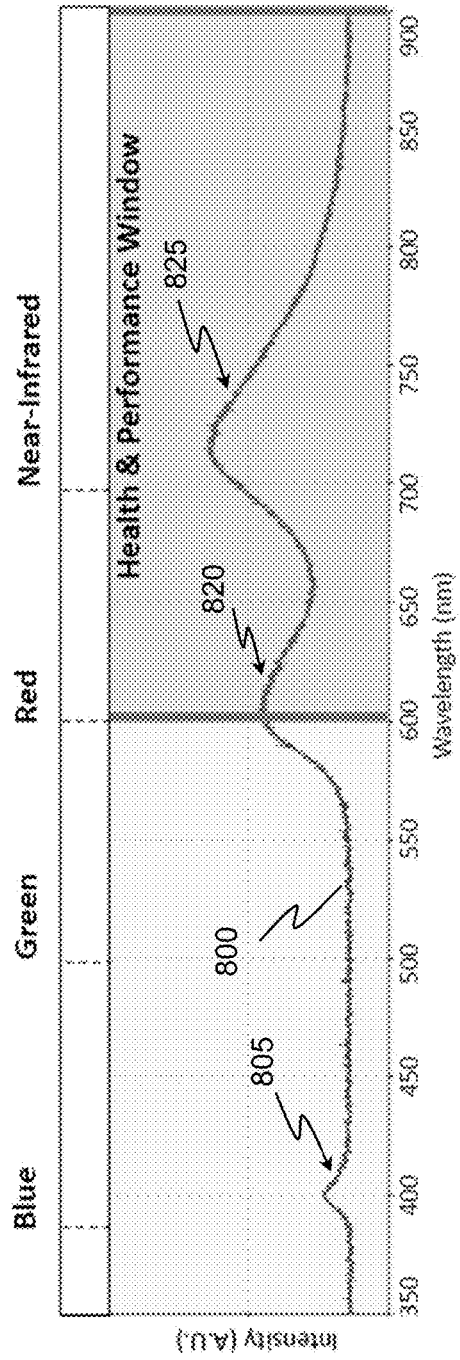

ELECTRICALLY PASSIVE LOW-LEVEL LIGHT THERAPY SYSTEM AND METHODS INCORPORATING SAME

RELATED APPLICATION DATA

This application is based on and claims priority under 37 U.S.C. § 119 to U.S. Provisional Application No. 62/720,544, filed Aug. 21, 2018, the entire contents of which are incorporated herein by reference.

FIELD OF THE DISCLOSURE

The present disclosure relates to a low-level light therapy system having an article of apparel that emits light in the visible/near infrared spectrum without using an electrical power source and a wearer of the article of apparel is exposed to the emitted light, and to systems and sub-systems that include the article of apparel. The emitted light in the visible/near infrared spectrum has a therapeutic effect and is useful in low-level light therapy methods. The present disclosure also relates to an article of apparel and other textile-based structures that emits light in the visible/near infrared spectrum per se, such as clothing, footwear, head covering, athletic gear, and bedding and towels.

BACKGROUND

In the discussion that follows, reference is made to certain structures and/or methods. However, the following references should not be construed as an admission that these structures and/or methods constitute prior art. Applicant expressly reserves the right to demonstrate that such structures and/or methods do not qualify as prior art against the present invention.

Light can affect the growth and metabolism of organisms (ranging from simple unicellular microorganisms to multicellular plants and mammals) and can produce a variety of beneficial therapeutic effects. Examples of well-known physiological effects are photosynthesis in plants and vitamin D production in mammals. Using light for therapeutic purposes, i.e., "light therapy," has evolved from using direct sunlight, to using filtered sunlight, to using artificial light. Early light therapy focused largely on using light in the ultraviolet (UV) range of the light spectrum to treat skin diseases, ulcers, syphilis, lupus, pellagra and tuberculosis, and to heal wounds.

Photo-biomodulation, an example biochemical mechanism that relates to mitochondrial cytochrome c oxidase (an endogenous photoreceptor), uses low power light—especially in the visible red to near infrared (NIR) wavelengths range—to affect the activity of one or more endogenous enzyme photoreceptors. Specifically, wavelengths of light used in photo-biomodulation are matched to the absorption spectra of photosensitive reagents, and therapeutic effects arise as a result of the energy absorbed in mammalian tissue. Visible red and NIR wavelengths are especially effective because they can penetrate deep into mammalian tissue and are primarily absorbed by hemoglobin and melanin. In contrast, ultraviolet light only penetrates into the surface of mammalian tissue, is primarily absorbed by DNA and proteins, and tends to be carcinogenic and mutagenic.

Current devices and systems that deliver light to a mammalian, for example, human, body for the purpose of providing Low Level Light Therapy (LLLT) do so via apparatuses that (1) contain actual lasers and/or LEDs and (2) use a physical electrical power source (primarily electrical outlets or batteries). Such requirements naturally limit the form of LLLT devices/systems and how and where LLLT devices/systems can be used and implemented. Thus, it would be beneficial to have systems, subsystems and components that can be used to provide LLLT that (a) are independent of an electrical power source and (b) produce visible and near infrared radiation independent of electrically powered radiation emission devices such as lasers, LEDs, and the like.

SUMMARY

The present disclosure is directed to low-level light therapy system(s) with an electrically passive, article of apparel that absorbs an incident spectrum including one or more of a UV wavelength, a visible wavelength, and a near infrared wavelength and emits light having an emission spectrum including visible light radiation and near infrared radiation. Light is emitted from a textile material consisting of a network of yarns (as well as the article of apparel incorporating such textile material) that emits light having an emission spectrum including visible light radiation and near infrared radiation in a direction toward a body of a person or any other mammalian species (such as a dog, a cat, or a horse) and, in particular, toward mammalian tissue such as human skin, where it imparts a therapeutic effect.

An exemplary embodiment of a low-level light therapy system comprises an article of apparel that absorbs an incident spectrum including one or more of a UV wavelength, a visible wavelength, and a near infrared wavelength and emits light having an emission spectrum including one or more of visible light radiation and near infrared radiation. The article of apparel is electrically passive, and the light having an emission spectrum including one or more of visible light radiation and near infrared radiation is emitted from the article of apparel in a direction toward a body of a person or any other mammalian species (such as a dog, a cat, or a horse) wearing the article of apparel.

An exemplary embodiment of a low-level light therapy sub-system comprises a textile material that absorbs an incident spectrum including one or more of a UV wavelength, a visible wavelength, and a near infrared wavelength and emits light having an emission spectrum including one or more of visible light radiation and near infrared radiation. The textile material is electrically passive, and the light having an emission spectrum including one or more of visible light radiation and near infrared radiation is emitted from the textile material in a direction toward a body of a person or any other mammalian species (such as a dog, a cat, or a horse).

An exemplary embodiment of a method of treating soft tissue in need thereof comprises exposing said tissue to the emission spectrum of the low-level light therapy system or light therapy sub-system.

An exemplary embodiment of a low-level light therapy method comprises exposing soft tissue to the emission spectrum of the low-level light therapy system or light therapy sub-system.

An exemplary embodiment of a method of manufacture comprises mixing a first textile grade, polymeric host material and at least one of a first fluorescent component and a second fluorescent component using extrusion techniques to form a masterbatch, wherein a concentration of the fluorescent component in the masterbatch is 2% to 20%, mixing the masterbatch with a volume of a second textile grade, polymeric host material to produce a feedstock in which a total amount of fluorescent component in the feedstock is 0.01 wt. % to 1 wt. %, processing the feedstock into flat yarn, and processing the flat yarn by texturing to form a textured yarn or by cutting to form a staple yarn. The first fluorescent component has a quantum efficiency of more than 90% for emission at visible wavelengths and the second fluorescent component has a quantum efficiency of more than 50% for emission at near infrared wavelengths, and when exposed to visible light, the textured yarn or staple yarn emits radiation having an emission spectrum including at least one peak in a range of 600 nm to 1200 nm.

BRIEF DESCRIPTION OF THE DRAWINGS

The foregoing summary, as well as the following detailed description of the embodiments, can be better understood when read in conjunction with the appended drawings. It should be understood that the embodiments depicted are not limited to the precise arrangements and instrumentalities shown.

FIGS. 7 to 10 show example articles of apparel.

FIGS. 11A to 11B are experimental results showing spectra of a fabric excited by blue light and green light (in arbitrary units of intensity versus wavelength (nm)).

FIGS. 13A to 13B are experimental results showing spectra of a fabric excited by blue light and green light (in arbitrary units of intensity versus wavelength (nm)).

DETAILED DESCRIPTION

Figure 1:
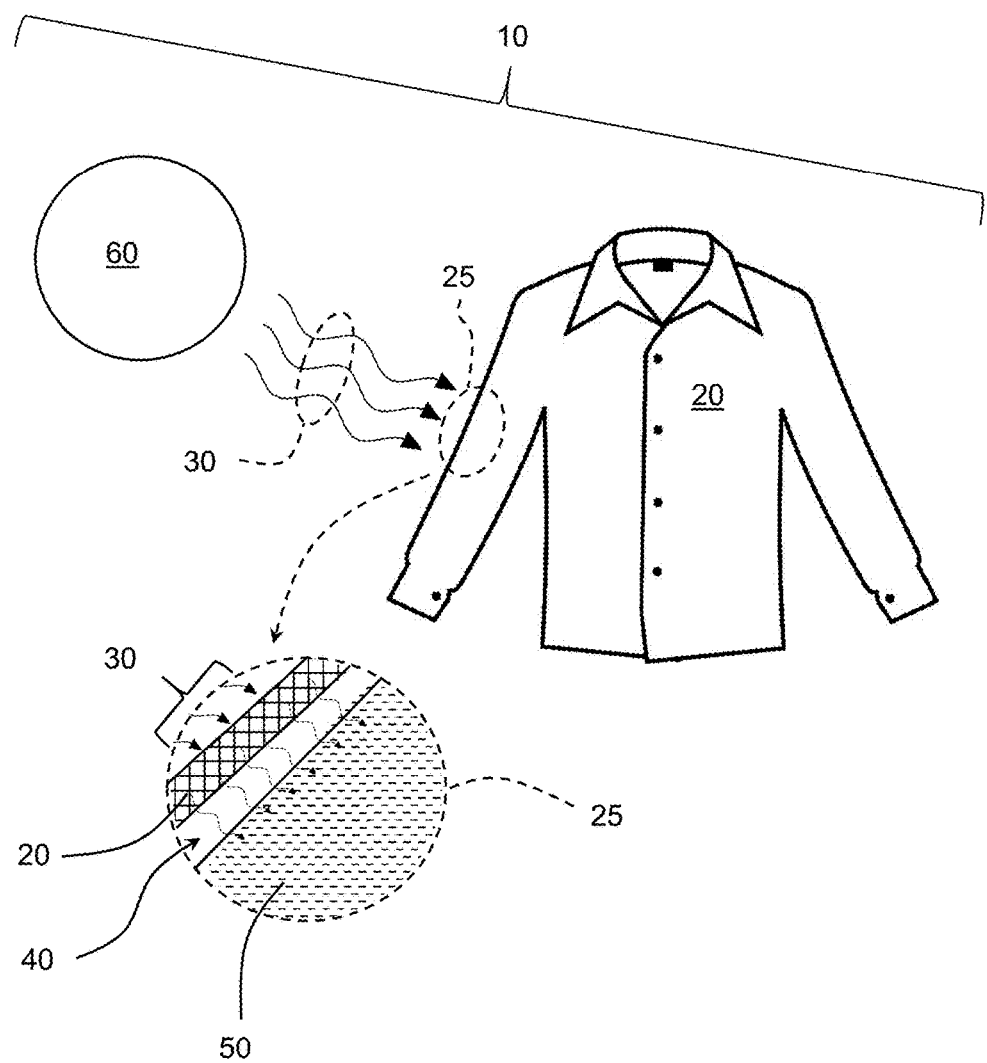
FIG. 1 schematically depicts an exemplary embodiment of a low-level light therapy system.

FIG. 1 shows a low-level light therapy system 10 that that absorbs an incident spectrum including one or more of a UV wavelength, a visible wavelength, and a near infrared wavelength and emits light having an emission spectrum including visible light radiation and near infrared radiation. In the example low-level light therapy system 10, an article of apparel 20 absorbs an incident spectrum 30 and emits light 40 in a direction toward a body 50 of a person wearing the article of apparel 20 (see magnified view 25 showing light 40 having an emission spectrum including one or more of visible light radiation and near infrared radiation is emitted from the article of apparel 20 in a direction toward a body 50 of a person wearing the article of apparel 20).

In exemplary embodiments, the incident spectrum 30 includes one or more of a UV wavelength (meaning radiation having wavelengths of 200 to 400 nm), a visible wavelength (meaning radiation having wavelengths of 400 to 700 nm), and a near infrared wavelength (meaning radiation having wavelengths of 700 to 1200 nm). The incident spectrum 30 originates in a source 60 that is external to the article of apparel 20. In some embodiments, the source 60 is a source of natural light and can include the sun, whether or not directly incident on the article of apparel 20. In alternative embodiments, the source 60 is an artificial source of a spectrum that replicates some or all of the spectrum emitted by the sun. In addition, the incident spectrum 30 from the source 60 can be filtered or otherwise directed and/or concentrated or moderated prior to the incident spectrum interacting with the article of apparel 20.

In exemplary embodiments, the article of apparel 20 absorbs at least a portion of the incident spectrum 30 and emits light 40 having an emission spectrum including one or more of visible light radiation (meaning radiation having wavelengths of 400 to 700 nm) and near infrared radiation (meaning radiation having wavelengths of 700 to 1200 nm). The emission spectrum includes at least one peak in a range of 600 nm to 1200 nm. For example, in exemplary embodiments, the emission spectrum includes one or more of a first peak between 700 nm and 800 nm with a full width at half maximum (FWHM) of 80 nm to 200 nm, alternatively 100 nm to 150 nm, and a second peak between 800 nm and 900 nm with a full width at half maximum (FWHM) of 80 nm to 200 nm, alternatively 100 nm to 150 nm.

Figure 2:
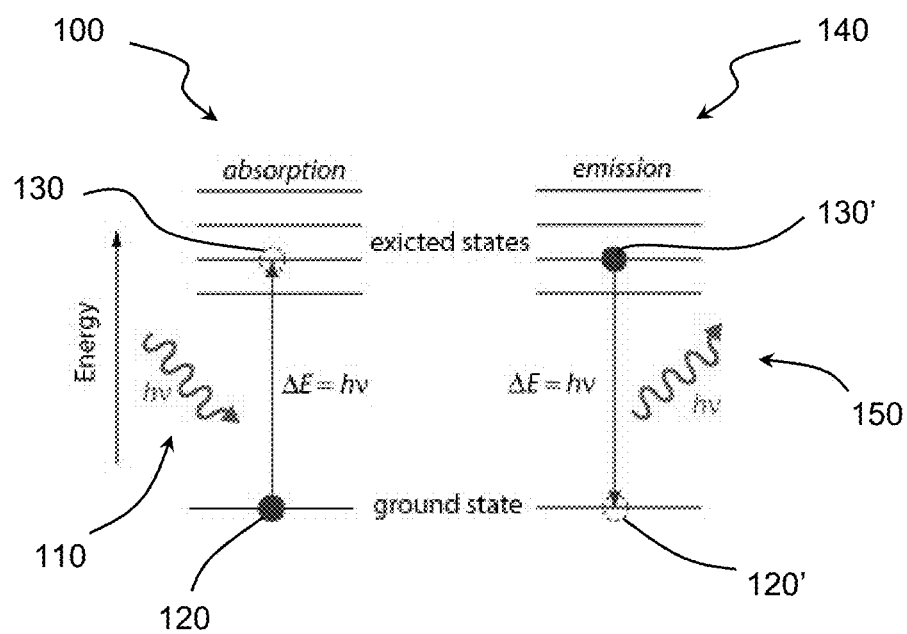
FIG. 2 schematically illustrates the process of absorption and emission.

In this context and as schematically illustrated in FIG. 2, the process of absorption 100 of at least a portion of the incident spectrum 30 includes incident radiation 110 interacting with a portion of the article of apparel 20 resulting in an electron be raised from a ground state 120 to an excited state 130. Subsequently, the process of emitting light (or emission) 140 includes the electron in the excited state 130' returns to the ground state 120' accompanied by emitted light 150.

The article of apparel 20 is electrically passive, meaning the article of apparel 20 does not directly utilize an external source of power and it requires a light source as the source of the incident spectrum 30 itself to emit the light 40 having the emission spectrum including one or more of visible light radiation and near infrared radiation. As one example, the source 60 can be the sun and the article of apparel has no external source of power; accordingly, only the energy in the incident spectrum 30 is provided to the low-level light therapy system 10. As a second example, the source 60 can be an electrically powered light source, such as a light bulb, providing a full spectrum that includes at least some wavelengths of 390 to 1200 nm and the article of apparel has no external source of power; accordingly, only the energy in the incident spectrum 30 is provided to the low-level light therapy system 10. As a third example, the source 60 can be an electrically powered light source, such as a light emitting diode (LED) with a spectrum that includes at least some wavelengths in the range of 200 to 1200 nm and the article of apparel has no external source of power; accordingly, only the energy in the incident spectrum 30 is provided to the low-level light therapy system 10.

Figures 3A, 3B:
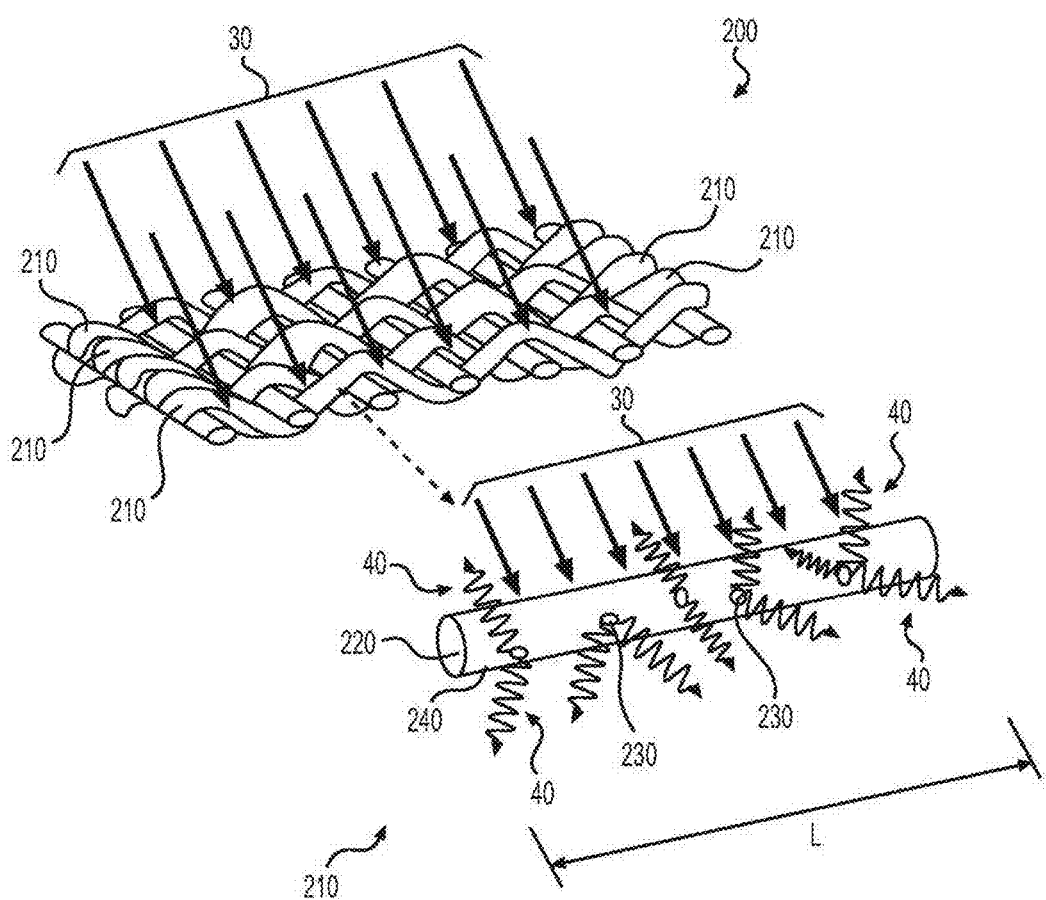
FIGS. 3A and 3B are magnified, schematic illustrations depicting a portion of an article of apparel (FIG. 3A) and an individual yarn (FIG. 3B) absorbing at least a portion of incident spectrum and emitting light having an emission spectrum.

FIG. 3A is a magnified, schematic illustration depicting a portion 200 of an article of apparel 20 absorbing at least a portion of incident spectrum 30 that includes one or more of a UV wavelength, a visible wavelength, and a near infrared wavelength and emitting light 40 having an emission spectrum including one or more of visible light radiation and near infrared radiation. As seen in FIG. 3A, the portion 200 of the article of apparel 20 includes one or more yarns 210. An individual yarn 210 is schematically depicted in FIG. 3B. Yarn 210 includes a textile grade, polymeric host material 220 and one or more fluorescent components 230. Incident spectrum 30 interacts with the yarn 210 (resulting in an electron being raised from a ground state to an excited state as previously described with reference to FIG. 2) and emitted light 40 having an emission spectrum (resulting from the electron in the excited state returning to the ground state as previously described with reference to FIG. 2) is subsequently emitted from the side surfaces 240 of the yarn 210. In being emitted from the side surfaces 240 of the yarn 210, the emission spectrum is emitted from a plurality of locations along a length (L) of the yarns 210.

Figure 4:
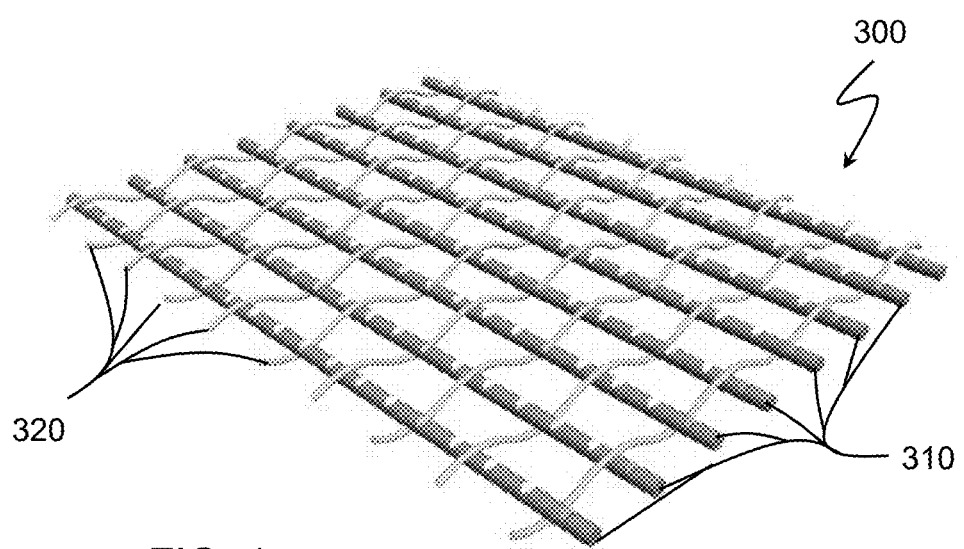
FIG. 4 is a schematic drawing of a network of yarns.

The yarns may be included in an article of apparel as a discrete yarn or a plurality of discrete yarns incorporated into a textile material, or as a plurality of similar or dissimilar yarns combined to form a network of yarns. FIG. 4 is a schematic drawing of a network of yarns 300. In exemplary embodiments, the network of yarns 300 includes a plurality of a first yarn type 310 and a plurality of a second yarn type 320. The different yarn types can be incorporated into the textile material in any suitable manner; for example, the weft yarns can be of a first yarn type and the warp yarns can be of a second yarn type. Either of the weft yarns or the warp yarns or both can be yarns that absorb an incident spectrum including one or more of a UV wavelength, a visible wavelength, and a near infrared wavelength and emits light having an emission spectrum including one or more of visible light radiation and near infrared radiation.

However, any, a subset, or all of the yarns in the network of yarns 300 can be yarns that absorb an incident spectrum including one or more of a UV wavelength, a visible wavelength, and a near infrared wavelength and emits light having an emission spectrum including one or more of visible light radiation and near infrared radiation. Accordingly, the network of yarns can incorporate one or more yarn types that absorb an incident spectrum including one or more of a UV wavelength, a visible wavelength, and a near infrared wavelength and emits light having an emission spectrum including one or more of visible light radiation and near infrared radiation, where different yarn types absorb different wavelengths from the incident spectrum and/or emit an emission spectrum with different wavelengths.

Figure 5:
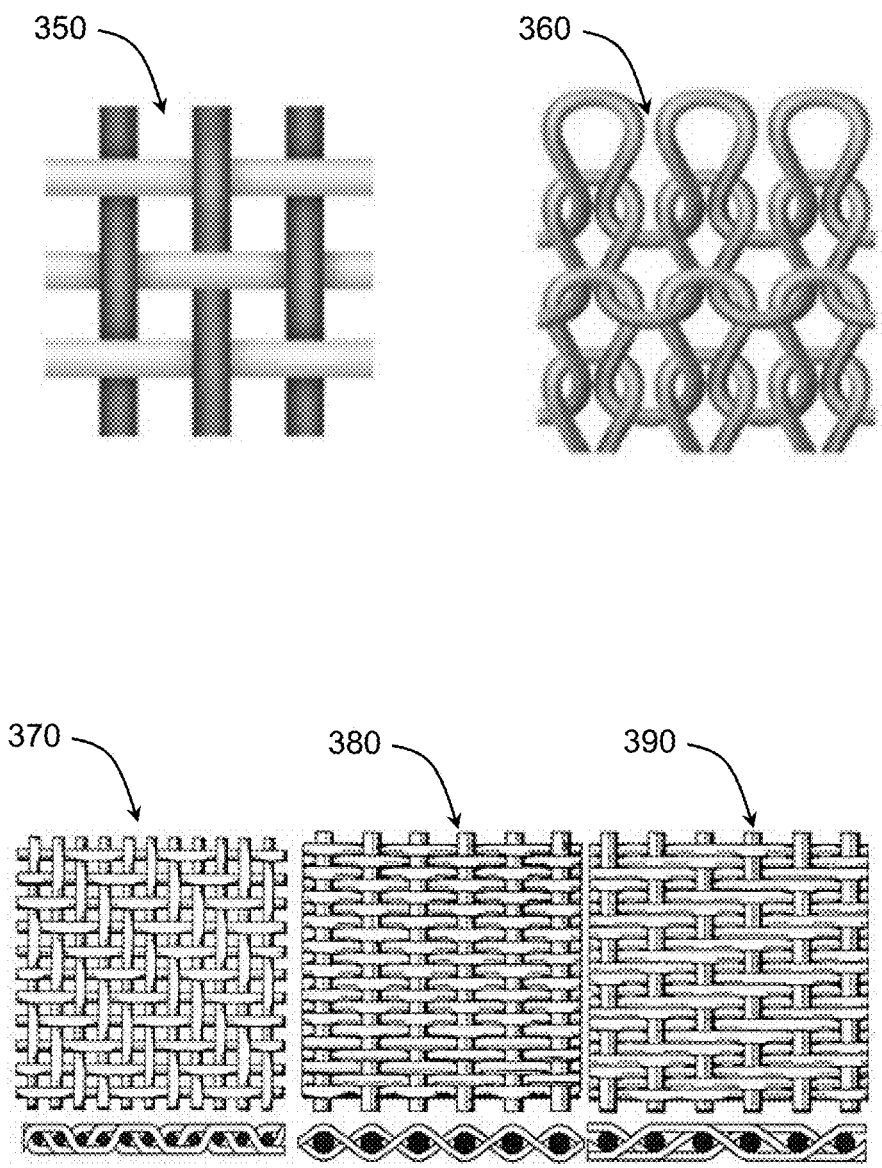
FIG. 5 illustrates examples of woven and knitted characteristics of the network of yarns.

The network of yarns can have any woven character and/or any knitted character. FIG. 5 illustrates an example of woven character 350, in which yarns are assembled in parallel using weaving, and an example of knitted character 360, in which yarns are knitted into a fabric. Other examples shown in FIG. 5 include twilled 370, plain dutch weave 380, and twilled dutch weave 390, but any woven or knitted character can be utilized in the low-level light therapy systems disclosed herein.

Figure 6:
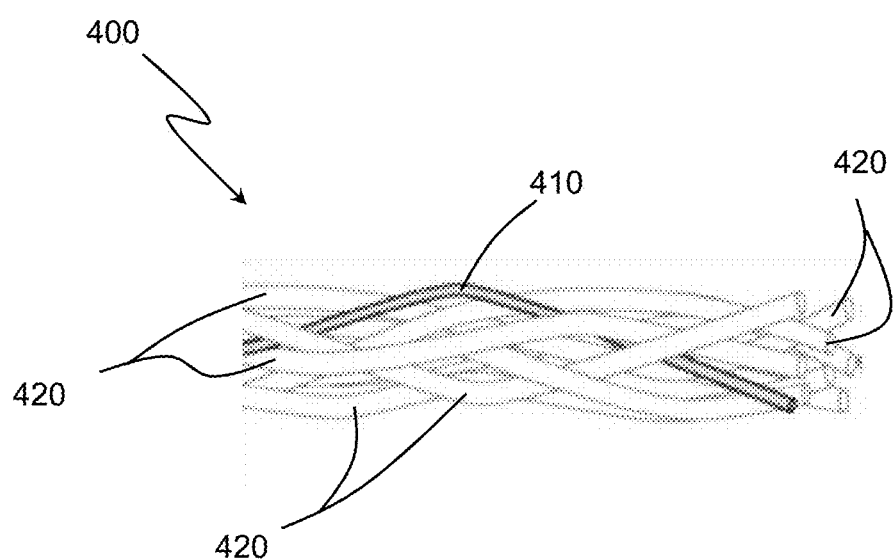
FIG. 6 is a schematic drawing of a multifilament yarn.
Figure 7:
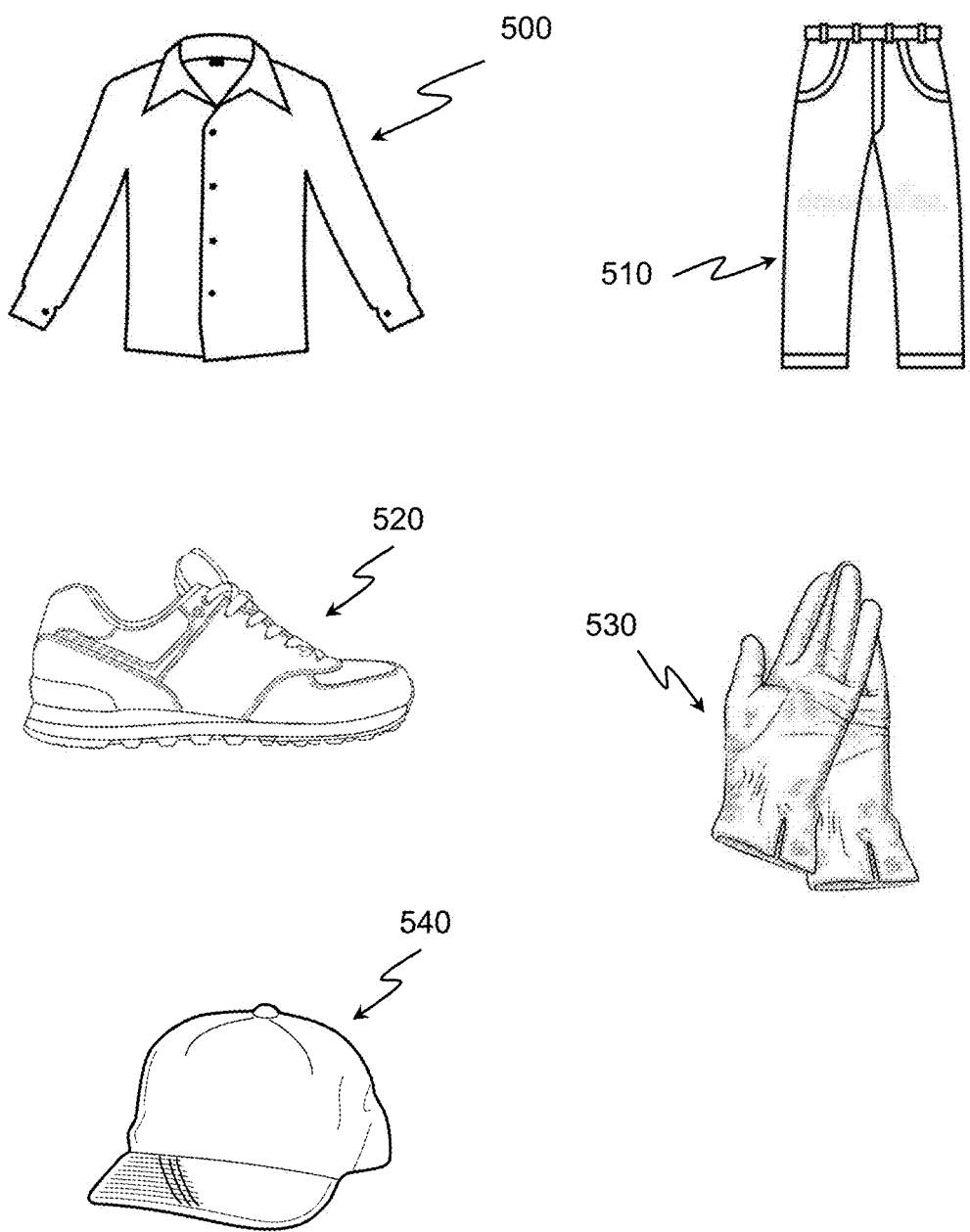

The yarns can be in any suitable form. For example, the yarns can be monofilament or multifilament, staple or continuous. FIG. 6 is a schematic drawing of a multifilament yarn 400. In exemplary embodiments, the multifilament yarn 400 includes at least one of a first filament type 410 and a plurality of a second filament type 420. The different filament types can be incorporated into the textile material in any suitable manner. The first filament type 410 absorbs an incident spectrum including one or more of a UV wavelength, a visible wavelength, and a near infrared wavelength and emits light having an emission spectrum including one or more of visible light radiation and near infrared radiation. One (or more than one) of such a first filament type 410 can be incorporated into the multifilament yarn 400. Alternatively, a majority of the filaments in the multifilament yarn 400 can be of such a first filament type 410. However, any, a subset, or all of the filaments in the multifilament yarn 400 can be of a type that absorb an incident spectrum including one or more of a UV wavelength, a visible wavelength, and a near infrared wavelength and emits light having an emission spectrum including one or more of visible light radiation and near infrared radiation. Accordingly, the multifilament yarn 400 can incorporate one or more filament types each of which absorb an incident spectrum including one or more of a UV wavelength, a visible wavelength, and a near infrared wavelength and emits light having an emission spectrum including one or more of visible light radiation and near infrared radiation, where different first filament types 420 absorb different wavelengths from the incident spectrum and/or emit an emission spectrum with different wavelengths.

In addition, the yarns can be staple or multi-filament, where staple refers to fiber of discrete length and multi-filament refers to a continuous fiber. Further, the yarns may be composite yarns with desired properties and aesthetics resulting from, for example, yarn mixes (mixed colors, mixed deniers, mixed cross-sections, mixed bicomponent/homofilament, etc.). Also for example, the yarns may be textured by, for example, forming crimps, loops, coils, or crinkles in the filaments, which affects the behavior and hand of textile materials made from them.

The yarns include a textile grade, polymeric host material 220. Suitable textile grade, polymeric host material 220 includes a homopolymer or a copolymer or a long-chain polymer selected from the group consisting of polyesters, polyamides, olefins, acrylics, poly(methyl methacrylate) (PMMA), polylactic acid (PLA), and polycarbonates. In exemplary embodiments, the textile grade, polymeric host material has an intrinsic viscosity (IV) in a range of 0.5 to 1.0 dL/g.

The yarns also include one or more fluorescent components. Example fluorescent components include one or more of a dye and a quantum dot.

The fluorescent component is characterized by having either or both an emission spectrum including visible light radiation having a quantum efficiency of 90% and above, and an emission spectrum in the near infrared range having a quantum efficiency of 50% and above. When the fluorescent component is a dye, the dye includes one or more of a perylene dye, a cyanine dye, a rhodamine dye, a coumarine dye, a dye belonging to the class of anthrapyridone dyes, thioxanthene dyes and thioindigoid dyes, or mixtures thereof.

In general, the higher the molecular weight of the fluorescent components, the less weight percent of the fluorescent components is necessary to obtain the desired intensity of emission spectrum. Also in general, the higher the quantum efficiency of the fluorescent components, the less weight percent of the fluorescent components is necessary to obtain the desired intensity of emission spectrum. Thus, in exemplary embodiments, the amount of fluorescent components in the textile grade, polymeric host material is in the range of 0.01 weight % (wt. %) to 1 wt. %. Alternatively, the amount of fluorescent components in the textile grade, polymeric host material is in the range of 0.01 wt. % to 0.1 wt. %, or is in the range of 0.05 wt. %, 0.10 wt. %, 0.15 wt. % or 0.20 wt. % to 0.10 wt. %, 0.25 wt. %, or 0.50 wt. %. In exemplary embodiments, 0.015 wt. % of a red anthrapyridone fluorescent dye was used, a combination of 0.025 wt. % of a perylene fluorescent dye and 0.06 wt. % of a cyanine fluorescent dye (which is a near infrared dye) was used, or a combination of 0.045 wt. % of a fluorescent dye called Vat Violet 3, which belongs to the class of thioindigoid dyes, and 0.045 wt. % of a cyanine fluorescent dye (which is a near infrared dye) was used.

Because of its strong UV light absorbing capabilities that competes with UV absorption capabilities of the fluorescent components, the amount of titanium dioxide ($TiO_2$) included in the yarns is minimized. In general, as the amount of titanium dioxide increase, the performance of the low level light therapy system decreases (as the absorption performance decreases). Thus, in exemplary embodiments, the amount of titanium dioxide is less than 2.0 wt. %, alternatively less than 1.0 wt. %. It is preferred that there be no titanium dioxide in the yarns, i.e., that the yarns are titanium dioxide free.

Individual yarns can be any desired cross-section. For example, individual monofilament yarn can have a circular cross-section and be, for example, on the order of 10 microns in diameter. Also for example, individual monofilament yarn can have a multilobal cross section, such as a trilobal cross section, and be, for example, on the order of 10 microns in diameter. Multifilament yarn can be of any type, including FFT (false twist textured) or AJT (air jet textured).

The yarns and fabrics or textile materials incorporating the yarns can be manufactured using suitable methods. For example, a first textile grade, polymeric host material and at least one of a first fluorescent component and a second fluorescent component can be mixed using extrusion techniques to form a masterbatch. In exemplary embodiments, the masterbatch has a concentration of the fluorescent component of 2% to 20%. The masterbatch is then mixed with a volume of a second textile grade, polymeric host material to produce a feedstock in which a total amount of fluorescent component in the feedstock is 0.01 wt. % to 1 wt. %, alternatively in the range of 0.05 wt. %, 0.10 wt. %, 0.15 wt. % or 0.20 wt. % to 0.10 wt. %, 0.25 wt. %, or 0.50 wt. %.

The feedstock is then processed into flat yarn. An example technique for processing the feedstock into flat yarn is melt spinning. But other techniques can be used, such as wet spinning or dry spinning. The flat yarn can be further processed by texturing to form a textured yarn or by cutting to form a staple yarn. Texturing the yarn helps to ensure light is emitted from the side surface along the length of the yarns (as described earlier with reference to FIG. 3B). As discloses elsewhere herein, when exposed to visible light, the textured yarn or staple yarn emits radiation having an emission spectrum including at least one peak in a range of 600 nm to 1200 nm. Texturing also serves secondary purposes including creating a softer and better touch ("hand feel") and improving moisture control.

Suitable textile grade, polymeric host materials and fluorescent components can be any such materials and components disclosed elsewhere herein. In exemplary embodiments, the textile grade, polymeric host material has an intrinsic viscosity (IV) in a range of 0.5 to 1.0 dL/g. In some exemplary embodiments, the first textile grade, polymeric host material and the second textile grade, polymeric host material are the same, i.e., compositionally identical. In other exemplary embodiments, the first textile grade, polymeric host material and the second textile grade, polymeric host material are of a same type of polymer, e.g., are both polyesters, polyamides, olefins, acrylics, PMMA, PLA, or polycarbonates. When the first textile grade, polymeric host material and the second textile grade, polymeric host material are not the same, i.e., not compositionally identical, it is preferable that the first textile grade, polymeric host material has a higher intrinsic viscosity (IV) than the second textile grade, polymeric host material.

In exemplary embodiments, the fluorescent components include one or more of a dye and a quantum dot and, when the fluorescent component is a dye, the dye includes one or more of a perylene dye, a cyanine dye, a rhodamine dye, a coumarine dye, a dye belonging to the class of anthrapyridone dyes, thioxanthene dyes and thioindigoid dyes, or mixtures thereof. In some exemplary embodiments, the first fluorescent component has a quantum efficiency of more than 90% for emission at visible wavelengths and the second fluorescent component has a quantum efficiency of more than 50% for emission at near infrared wavelengths.

It should be noted that prior to mixing, the optically clear, polymeric host material can be processed using conventional pretreatment, drying and crystallization techniques. Also, the manufactured textured yarn or staple yarn can be further manufactured into fabrics or textile materials or an article of apparel using suitable methods known in the textile industry.

As described herein, the fluorescent components emit light at visible or near infrared wavelengths. The fluorescent components transform part of the wideband incident ambient light into narrow band light with the precise wavelengths that studies have shown to have wellness and therapeutic benefits such as for hair regrowth, weight loss, muscle toning, skin rejuvenation, and several other treatments. The following Table 1 presents effective wavelengths for Low Level Light Therapy ("LLLT") for certain applications.

TABLE 1

| Application | Effective Wavelength |
| --- | --- |
| Cellulite | 600-900 nm |
| Skin | 600-900 nm |
| Weight loss | 600-900 nm |
| Acupuncture | 600-900 nm |
| Hair Growth | 600-750 nm |
| Pain | 600-900 nm |
| Bone regeneration | 600-900 nm |
| Blood Flow | 300-900 nm |
| Muscle relaxation (muscle-ache) | 600-900 nm |
| Sport injuries | 600-900 nm |
| Cartilage growth | 600-900 nm |

The Bunsen-Roscoe law (reciprocity law) states that the quantity of the reaction of a photochemical reaction is proportional to the product of light irradiance and exposure time. Most photo-biomodulation effects are cumulative and research has shown that positive results depend on the administered dose of light rather than the intensity alone. In other words, the same dose (and same effect) can be provided by a high intensity of light in a short time or a low intensity of light in a long time. Accordingly, the low-level light therapy systems disclosed herein can be used in methods of treating soft tissue and as a low-level light therapy method in which soft tissue is exposed to the emission spectrum of the low-level light therapy system. In particular, the fluorescent components utilized in the yarns that are incorporated into the article of apparel and/or the textile material that are part of the low-level light therapy system and/or sub-systems are selected to produce an emission spectrum that includes one or more of the effective wavelengths set forth in Table 1. Moreover, the time exposure to an emission spectrum that includes one or more of the effective wavelengths may be much longer than the typical time exposure involved in conventional low-level light therapy (such as conventional light therapy using LEDs and laser sources). Because the time of exposure can be longer using the structures disclosed herein, the intensity of the emission spectrum that includes one or more of the effective wavelengths emitted from such structures does not need to be high to provide an effective light dosage.

Low-level light therapy systems disclosed herein can be used to apply light therapy to contribute to a wide range of therapeutic effects at the molecular, cellular, psychosomatic, psychological and tissue levels.

Light therapy (in particular, Low Level Light Therapy ("LLLT")) is an increasingly recognized and recommended treatment option for prevention, therapy, and rehabilitation. Common applications of LLLT are wound healing, pain management, inflammation and restoration of function, treatment of skin disease and skin rejuvenation, hair loss and hair regrowth, chronic ulcers and chronic pain syndromes like headaches, dermatology (for example, LLLT was approved by the Food and Drug Administration in 2007 for the treatment of mild to moderate male pattern hair loss), acne therapy, and photo-rejuvenation (to reverse the process of sun-induced aging and environmental damage to skin).

As used herein, "low-level" used in conjunction with "low-level light therapy" and "LLLT" refers to light sources having a power density output that is less than or equal to 100 mW/cm$^2$. These low level light sources can provide enhanced cellular function as therapeutic effect through the physiological effect of photo-biomodulation. Given their low power density, low-level light therapy is not used for surgery or tissue ablation due to the low power density employed. In contrast, light sources with output power density larger than 100 mW/cm$^2$ are called high-level light ("HLL"). High-level light sources cause a photothermal physiological effect and cellular destruction, and, given their high power density, these high-level light sources are used for surgery and ablation.

In exemplary embodiments, the emitted light mimics the absorption spectrum of the molecules that are absorbing the light, and the wavelengths that are strongly absorbed can also enable a photobiological response. For example, visible light can affect the human immune system response through the skin. Skin is naturally exposed to light more than other organs and responds well to red and near infrared wavelengths. Thus, an emission spectrum that includes visible light, and preferably red and near infrared wavelengths, can penetrate epidermal and dermal layers to a depth of 2-3 mm and directly interact with circulating lymphocytes to modulate immune system function.

In other embodiments, mitochondria (which have absorption peaks in the red and near infrared regions of the electromagnetic spectrum) synthesize nitric oxide (NO) in response to light therapy by neuronal nitric oxide synthase and this nitric oxide then contributes to regulating respiration by competitive binding to the oxygen binding of cytochrome c oxidase to thereby affect cell metabolism.

In still other embodiments, emitted light in the visible light range, i.e., 600 nm to 700 nm, can penetrate epidermal and dermal layers and directly interact with circulating lymphocytes to modulate the immune function (resulting in enhanced phagocyte activity of monocytes and granulocytes and the proliferation of other human cells). Visible light is also the most powerful external regulator of the circadian response.

In further embodiments, emitted light having red and infrared wavelengths can been used for a variety of therapeutic applications, including: healing wounds, treating mouth sores caused by radiation and chemotherapy, re-growing hair, recovering from cosmetic surgery, treating injuries to joints and soft tissue, reducing the inflammatory pain of arthritis, and carpal tunnel syndrome, among others. Emitted light having red wavelengths can be used to stimulate the regrowth of nerve cells. Emitted light having red and infrared wavelengths helps with blood circulation and natural healing by stimulating DNA synthesis in human peripheral blood lymphocytes but also induces a change in the cytokine content in the blood. These wavelengths of light penetrate skin cells stimulating production of antioxidants, reducing cellular stress and increasing cellular energy in the form of adenosine triphosphate (ATP).

In still further embodiments, emitted light having long infrared wavelengths allow for deeper tissue penetration than visible wavelengths. Near infrared light (600-1200 nm) can penetrate human tissue for over an inch and transcutaneously deliver deep into inner tissues such as muscles and nerves.

In still other embodiments, emitted light having visible and infrared wavelengths can penetrate the circulating blood, suggesting such low-level light therapy systems can be used to apply light therapy for blood related therapeutic effects.

It should be noted that penetration depths disclosed herein can be contingent on tissue type, pigmentation and foreign substances on the skin surface but, nonetheless, can be generally understood to have the following characteristics: visible light in the blue-green range (475-545 nm) can penetrate twice as far as ultraviolet (UV) light (150-380 nm), while red and near Infrared (NIR) light (600-1200 nm) can penetrate more than ten times as far as UV light. Emitted light with a wavelength between 600 and 1200 nm constitutes the so-called therapeutic window because these wavelengths can penetrate into the subcutaneous tissue without significant absorption by water.

The low-level light therapy system can be embodied in any suitable article of apparel. Such apparel can be made with yarns that are embedded with fluorescent components (dyes and/or quantum dots). The fluorescent components can emit light at visible or near infrared wavelengths and transform part of the wideband incident ambient light into narrow band light with the precise wavelengths that studies have shown to have wellness and therapeutic benefits such as for hair regrowth, weight loss, muscle toning, skin rejuvenation, and several other treatments as disclosed herein.

Several example articles of apparel are illustrated in FIGS. 7 to 10. For example, the article of apparel can be clothing, such as a shirt 500, a pant 510, a short, a sock. Other suitable articles of clothing include a footwear 520, a hand covering, such as glove 530, a wrist band, a head band, and a head covering, which includes, for example, a hat 540, a scarf, or a helmet. In addition, suitable articles of clothing include athletic gear such as work out clothing 600 and uniforms. Further, the low-level light therapy system can be embodied in all or a portion of any suitable article of apparel, such as an arm sleeve, a calf sleeve, an arm band 610, or bandage material. The low-level light therapy system can also be embodied in all or a portion of any suitable article of apparel 620 used for other mammals, such as dogs, cats or horses.

In addition to all or a portion of articles of apparel, the low-level light therapy system can be incorporated into bedding or a towel.

When a plurality of yarns is incorporated into a textile material, the emission from the side surface at substantially multiple points thought the yarn, i.e., light is absorbed and emitted locally at discreet points (see, e.g., FIG. 3B) results in area of the textile material emitting the emission spectrum. This area can be the entire article of apparel or can be a plurality of discreet areas within the article of apparel. In some embodiments, the plurality of discreet areas can be located within the article of apparel to correspond to discreet body parts. For example, where the article of apparel is a shirt, the plurality of discreet areas can be located within the shirt to correspond to the discreet body parts of any one or more of a shoulder, an elbow, a bicep, a tricep, etc. In another example, where the article of apparel is a pant or a short, the plurality of discreet areas can be located within the pant or a short to correspond to the discreet body parts of any one or more of a knee, a hip, a quadriceps, a hamstring, etc. In still another example, where the article of apparel is a headgear, the plurality of discreet areas can be located within the headgear to correspond to the discreet body parts of any one or more of a forehead, a crown, a temple, etc.

Although described herein in connection with an article of apparel, such as clothing, footwear, head covering, and athletic gear, it should be understood that the structure and methods and principles disclosed herein can be similarly applied to other textile-based objects, such as bedding and towels, and sun shade structures. In each instance, the textile-based objects can absorb an incident spectrum and, when the textile-based object is oriented toward a body of a person, can emit light in a direction toward the body of that person. For bedding and towels, that can mean a person swaddled, draped, or cloaked in the textile-based object can receive the light emitted from the textile-based object; for sun shade structures, that can mean a person sitting underneath or in the shade of such a structure can receive the light emitted from the textile-based object.

The textile materials may be implemented in conjunction with other existing special performance textile technologies, like geotextiles, nanotechnology textiles, push/pull fabric constructions, phase change material (PCM) textiles, temperature/humidity gradient textiles, etc., designed for applications like moisture management, waterproofing, comfort cooling, and comfort heating. Functional finishes and coatings for antimicrobial, antistatic, crease-resistance, flame-resistance, water and oil repellency, waterproofing, etc., are all also compatible with the textile materials and can provide additional properties without affecting the performance of the textile materials, as well as articles of apparel comprising such textile materials, themselves.

Further, a secondary property of the articles of apparel is a "shading" effect whereby the yarns/fabric do not heat up under the sun as much as would conventionally be expected because the use of fluorescent components with high quantum efficiency results in yarns that release most of the absorbed energy via the production of therapeutic emitted light and is not retained as heat-producing energy. An additional secondary effect is extra protection against short wavelengths having damaging effect on the human skin, which occurs by converting the energy in the potentially damaging, short wavelengths into energy at more useful, less damaging, and/or therapeutic emitted light wavelengths.

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1

A fabric was constructed using yarns made from textile—grade polyester (PET) with IV=0.65 dL/g. The PET is "super bright," i.e., it contains 0.00% titanium dioxide. The yarn includes 0.015 wt. % of a red anthrapyridone fluorescent dye called "solvent red dye 149" that is distributed homogenously in the PET polymeric host material. The fabric was stretched taut and, in separate experiments, exposed to a first spectrum (700 in FIG. 11A) containing blue light with a peak (705 in FIG. 11A) at 450 nm and exposed to a second spectrum (710 in FIG. 11B) containing green light with a peak (715 in FIG. 11B) at 525 nm.

FIG. 11A shows that the fabric exposed to the first spectrum 700 emits a spectrum of red light with a peak (725 in FIG. 11A) at 670 nm and a full width at half maximum (FWHM) of about 85 nm. FIG. 11B shows that the fabric exposed to the second spectrum 710 also emits a spectrum of red light with a peak (725 in FIG. 11B) at 670 nm and a full width at half maximum (FWHM) of about 82.5 nm. In both instances, the peak of 670 nm for the emitted light is a therapeutic wavelength within the health and performance window.

From FIGS. 11A and 11B, one can observe the following. First, the peak wavelength in the emitted spectrum is independent of the incident spectrum 700,710 (as both a peak at 450 nm and a peak at 525 nm in the incident spectra 700,710 resulted in an emission spectrum with a peak at 670 nm). Second, although the first spectrum 700 containing incident blue light with a peak at 450 nm was approximately double the magnitude of the second spectrum 710 containing incident green light with a peak at 525 nm, the emission peak at 670 nm for the emitted spectrum in each experiment had approximately the same magnitude.

Example 2

A fabric was constructed using yarns made from textile—grade polyester (PET) with IV=0.65 dL/g. The PET is "super bright," i.e., it contains 0.00% titanium dioxide. The yarn includes 0.025 wt. % of a perylene fluorescent dye and 0.06 wt. % of a cyanine fluorescent dye (which is a near infrared dye), both of which are distributed homogenously in the PET polymeric host material. The fabric was stretched taut and, in separate experiments, exposed to a first spectrum (750 in FIG. 12A) containing blue light with a peak (755 in FIG. 12A) at 390 nm, exposed to a second spectrum (760 in FIG. 12B) containing green light with a peak (765 in FIG. 12B) at 525 nm, and exposed to a third spectrum (770 in FIG. 12C) containing red light with a peak (775 in FIG. 12C) at 630 nm.

Figure 12A:
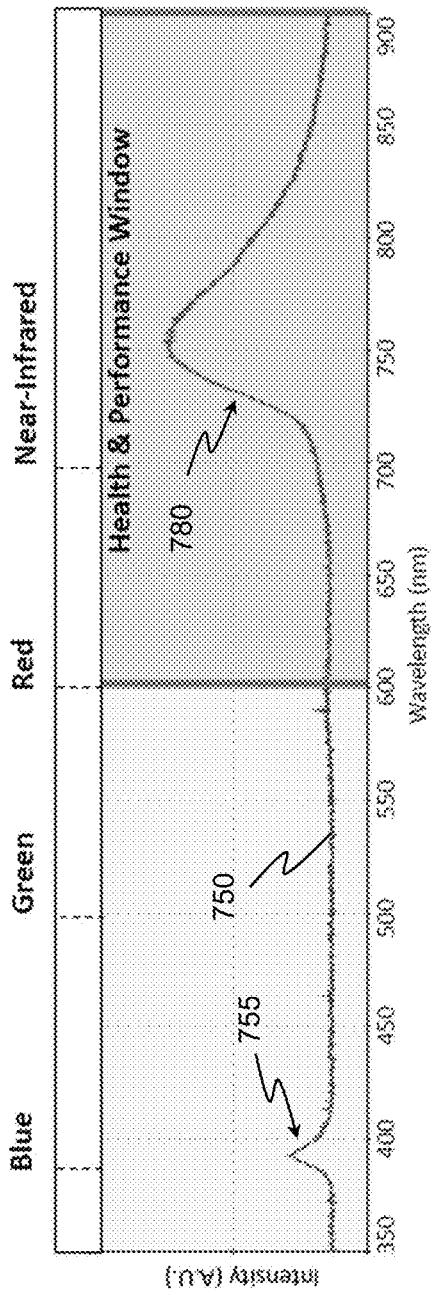
FIGS. 12A to 12C are experimental results showing spectra of a fabric excited by blue, green and red light (in arbitrary units of intensity versus wavelength (nm)).
Figure 12B:
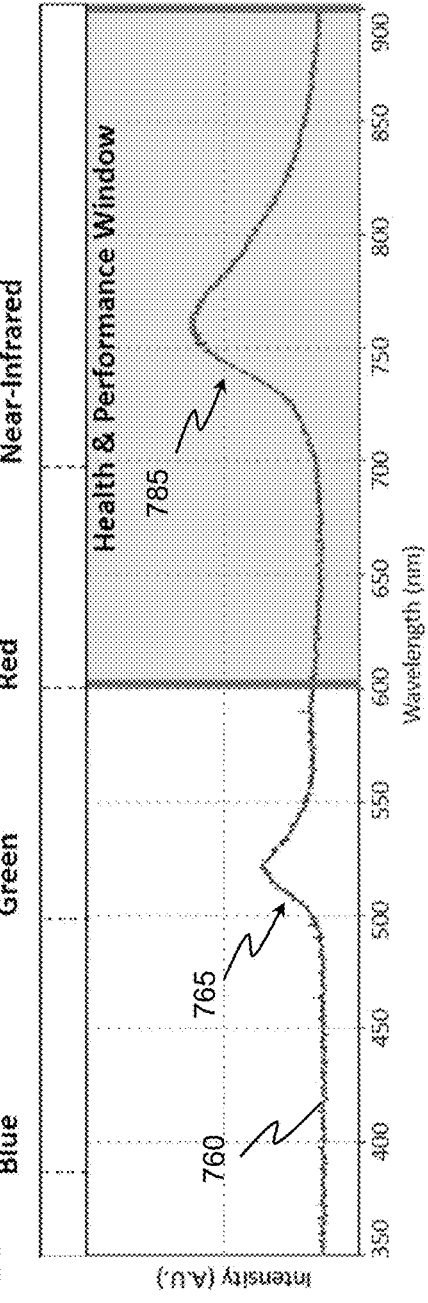
Figure 12C:
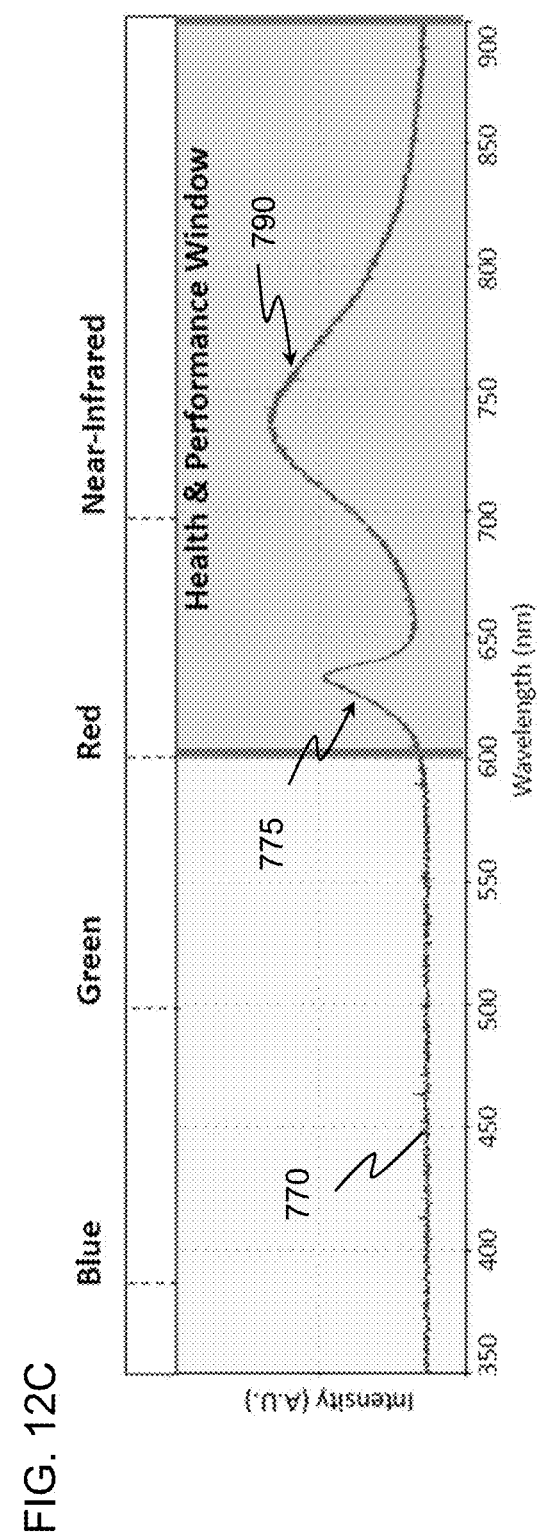

FIG. 12A shows that the fabric exposed to the first spectrum 750 emits a spectrum of near infrared (NIR) light with a peak (780 in FIG. 12A) at 756 nm and a full width at half maximum (FWHM) of about 85 nm. FIG. 12B shows that the fabric exposed to the second spectrum 760 also emits a spectrum of NIR light with a peak (785 in FIG. 12B) at 756 nm and a full width at half maximum (FWHM) of about 86 nm. FIG. 12C shows that the fabric exposed to the third spectrum 770 also emits a spectrum of NIR light with a peak (790 in FIG. 12C) at 745 nm and a full width at half maximum (FWHM) of about 103 nm. In each instance, the peak of 750±6 nm for the emitted light is a therapeutic wavelength within the health and performance window.

Example 3

A fabric was constructed using yarns made from textile—grade polyester (PET) with IV=0.65 dL/g. The PET is "super bright," i.e., it contains 0.00% titanium dioxide. The yarn includes 0.045 wt. % of a fluorescent dye called Vat Violet 3, which belongs to the class of thioindigoid dyes, and 0.045 wt. % of a cyanine fluorescent dye (which is a near infrared dye), both of which are distributed homogenously in the PET polymeric host material. The fabric was stretched taut and, in separate experiments, exposed to a first spectrum (800 in FIG. 13A) containing blue light with a peak (805 in FIG. 13A) at 400 nm, and exposed to a second spectrum (810 in FIG. 13B) containing green light with a peak (815 in FIG. 13B) at 525 nm.

FIG. 13A shows that the fabric exposed to the first spectrum 800 emits a spectrum with two peaks—a first peak (820 in FIG. 13A) at 600 nm and a full width at half maximum (FWHM) of about 75 nm and a second peak (825 in FIG. 13A) at 730 nm and a full width at half maximum (FWHM) of about 113 nm. The first peak 820 is a red emission peak and the second peak 825 is a NIR emission peak.

FIG. 13B shows that the fabric exposed to the second spectrum 810 emits a spectrum of with two peaks—a first peak (830 in FIG. 13B) at 600 nm and a full width at half maximum (FWHM) of about 75 nm and a second peak (835 in FIG. 13B) at 730 nm and a full width at half maximum (FWHM) of about 125 nm. The first peak 830 is a red emission peak and the second peak 835 is a NIR emission peak.

The spectra shown in FIGS. 11A-B, 12A-C, and 13A-B are presented graphically as arbitrary units of intensity versus wavelength in nm and, in each graph, intensity (arbitrary units) on the y-axis ranges from zero to 10000 arbitrary units and wavelength on the x-axis ranges from 350 nm to 900 nm.

While reference has been made to specific embodiments, it is apparent that other embodiments and variations can be devised by others skilled in the art without departing from their spirit and scope. The appended claims are intended to be construed to include all such embodiments and equivalent variations.

What is claimed is:

1. A low-level light therapy system, comprising:
    an article of apparel that absorbs an incident spectrum including one or more of a UV wavelength, a visible wavelength, and a near infrared wavelength and emits light having an emission spectrum including one or more of visible light radiation and near infrared radiation,
    wherein the article of apparel is electrically passive,
    wherein the light having an emission spectrum including one or more of visible light radiation and near infrared radiation is emitted from the article of apparel in a direction toward a body of a person wearing the article of apparel, and
    wherein the emission spectrum includes one or more of a first peak between 700 nm and 800 nm with a full width at half maximum (FWHM) of 100 nm to 150 nm and a second peak between 800 nm and 900 nm with a full width at half maximum (FWHM) of 100 nm to 150 nm.

2. The light therapy system according to claim 1, wherein the article of apparel, comprises:
    a textile material including a network of yarns, wherein the yarns include one or more of a textured yarn and a staple yarn;
    wherein each yarn in the network of yarns includes a textile grade, polymeric host material and 0.01 wt. % to 1.0 wt. % of one or more fluorescent components,
    wherein the fluorescent component having an emission spectrum including visible light radiation has a quantum efficiency of 90% and above, and
    wherein the fluorescent component having an emission spectrum in the near infrared range has a quantum efficiency of 50% and above.

3. The light therapy system according to claim 2, wherein the fluorescent component includes one or more of a dye and a quantum dot.

4. The light therapy system according to claim 3, wherein the dye includes one or more of a perylene dye, a cyanine dye, a rhodamine dye, a coumarine dye, and a dye belonging to the class of anthrapyridone dyes, thioxanthene dyes and thioindigoid dyes.

5. The light therapy system of claim 3, wherein the dye includes one or more species of fluorescent dyes.

6. The light therapy system according to claim 2, wherein the textile grade, polymeric host material is a homopolymer or a copolymer or a long-chain polymer and is selected from the group consisting of polyesters, polyamides, olefins, acrylics, PMMA, PLA, and polycarbonates, and wherein the textile grade, polymeric host material has an intrinsic viscosity (IV) in a range of 0.5 to 1.0 dL/g.

7. The light therapy system according to claim 6, wherein each yarn in the network of yarns further includes less than 2.0 wt. % titanium dioxide.

8. The light therapy system according to claim 2, wherein the light having an emission spectrum including one or more of visible light radiation and near infrared radiation emitted from the article of apparel is emitted from a plurality of locations along a length of one or more of the yarns.

9. The light therapy system according to claim 1, wherein the emission spectrum includes at least one peak in a range of 600 nm to 1200 nm.

10. The light therapy system according to claim 1, wherein the light having an emission spectrum including one or more of visible light radiation and near infrared radiation is emitted from a portion of the article of apparel.

11. The light therapy system according to claim 1, wherein the article of apparel is selected from the group consisting of a footwear, a shirt, a pant, a short, a hand covering, a sock, an arm sleeve, a calf sleeve, an arm band, a wrist band, a head band, and a head covering.

12. The light therapy system according to claim 11, wherein the head covering is a hat or a helmet.

13. The light therapy system according to claim 1, wherein the article of apparel is an athletic gear.

14. The light therapy system according to claim 1, further comprising a source that emits the incident spectrum.

15. The light therapy system of claim 1, wherein the article of apparel, comprises:
    a plurality of yarns, wherein the yarns include one or more of a textured yarn and a staple yarn;
    wherein each yarn includes a textile grade, polymeric host material and 0.01 wt. % to 1.0 wt. % of one or more fluorescent components,
    wherein the fluorescent component having an emission spectrum including visible light radiation has a quantum efficiency of 90% and above, and
    wherein the fluorescent component having an emission spectrum in the near infrared range has a quantum efficiency of 50% and above.

16. The light therapy system according to claim 15, wherein the dye includes one or more of a perylene dye, a cyanine dye, a rhodamine dye, a coumarine dye, and a dye belonging to the class of anthrapyridone dyes, thioxanthene dyes and thioindigoid dyes.

17. The light therapy system according to claim 16, wherein the textile grade, polymeric host material is a homopolymer or a copolymer or a long-chain polymer and is selected from the group consisting of polyesters, polyamides, olefins, acrylics, PMMA, PLA, and polycarbonates, and wherein the textile grade, polymeric host material has an intrinsic viscosity (IV) in a range of 0.5 to 1.0 dL/g.

18. The light therapy system according to claim 17, wherein each yarn in the network of yarns further includes less than 2.0 wt. % titanium dioxide.

19. The light therapy system according to claim 18, wherein the light having an emission spectrum including one or more of visible light radiation and near infrared radiation emitted from the article of apparel is emitted from a plurality of locations along a length of one or more of the yarns.

20. The light therapy system according to claim 19, wherein the emission spectrum includes at least one peak in a range of 600 nm to 1200 nm.

21. The light therapy system according to claim 19, wherein the emission spectrum includes one or more of a first peak between 700 nm and 800 nm with a full width at half maximum (FWHM) of 100 nm to 150 nm and a second peak between 800 nm and 900 nm with a full width at half maximum (FWHM) of 100 nm to 150 nm.

22. The light therapy system according to claim 18, wherein the light having an emission spectrum including one or more of visible light radiation and near infrared radiation is emitted from a portion of the article of apparel.

23. The light therapy system according to claim 22, wherein the article of apparel is selected from the group consisting of a footwear, a shirt, a pant, a short, a hand covering, a sock, an arm sleeve, a calf sleeve, an arm band, a wrist band, a head band, and a head covering.

24. The light therapy system according to claim 22, wherein the article of apparel is an athletic gear.

25. The light therapy system according to claim 18, further comprising a source that emits the incident spectrum.

26. A low-level light therapy system, comprising:
an article of apparel that absorbs an incident spectrum including one or more of a UV wavelength, a visible wavelength, and a near infrared wavelength and emits light having an emission spectrum including one or more of visible light radiation and near infrared radiation,
wherein the article of apparel is electrically passive,
wherein the light having an emission spectrum including one or more of visible light radiation and near infrared radiation is emitted from the article of apparel in a direction toward a body of a person wearing the article of apparel,
wherein the article of apparel, comprises a textile material including a network of yarns, wherein the yarns include one or more of a textured yarn and a staple yarn,
wherein each yarn in the network of yarns includes a textile grade, polymeric host material and 0.01 wt. % to 1.0 wt. % of one or more fluorescent components,
wherein the fluorescent component having an emission spectrum including visible light radiation has a quantum efficiency of 90% and above,
wherein the fluorescent component having an emission spectrum in the near infrared range has a quantum efficiency of 50% and above,
wherein the textile grade, polymeric host material is a homopolymer or a copolymer or a long-chain polymer and is selected from the group consisting of polyesters, polyamides, olefins, acrylics, PMMA, PLA, and polycarbonates, and wherein the textile grade, polymeric host material has an intrinsic viscosity (IV) in a range of 0.5 to 1.0 dL/g, and
wherein each yarn in the network of yarns further includes less than 2.0 wt. % titanium dioxide.

27. The light therapy system according to claim 26, wherein the fluorescent component includes one or more of a dye and a quantum dot.

28. The light therapy system according to claim 27, wherein the dye includes one or more of a perylene dye, a cyanine dye, a rhodamine dye, a coumarine dye, and a dye belonging to the class of anthrapyridone dyes, thioxanthene dyes and thioindigoid dyes.

29. The light therapy system of claim 27, wherein the dye includes one or more species of fluorescent dyes.

30. The light therapy system according to claim 26, wherein the light having an emission spectrum including one or more of visible light radiation and near infrared radiation emitted from the article of apparel is emitted from a plurality of locations along a length of one or more of the yarns.

31. The light therapy system according to claim 30, wherein the emission spectrum includes one or more of a first peak between 700 nm and 800 nm with a full width at half maximum (FWHM) of 100 nm to 150 nm and a second peak between 800 nm and 900 nm with a full width at half maximum (FWHM) of 100 nm to 150 nm.

32. The light therapy system according to claim 31, wherein the light having an emission spectrum including one or more of visible light radiation and near infrared radiation is emitted from a portion of the article of apparel.

33. The light therapy system according to claim 26, wherein the emission spectrum includes at least one peak in a range of 600 nm to 1200 nm.

34. The light therapy system according to claim 26, wherein the article of apparel is selected from the group consisting of a footwear, a shirt, a pant, a short, a hand covering, a sock, an arm sleeve, a calf sleeve, an arm band, a wrist band, a head band, and a head covering.

35. The light therapy system according to claim 34, wherein the head covering is a hat or a helmet.

36. The light therapy system according to claim 26, wherein the article of apparel is an athletic gear.

37. The light therapy system according to claim 26, further comprising a source that emits the incident spectrum.

* * * * *